United States Patent [19]

Davallou

[11] Patent Number: 5,709,222
[45] Date of Patent: Jan. 20, 1998

[54] BODY WASTE DETECTION AND ALARM SYSTEM

[76] Inventor: Harry H. Davallou, P.O. Box 2629, La Jolla, Calif. 92038

[21] Appl. No.: 779,686

[22] Filed: Jan. 7, 1997

[51] Int. Cl.$^6$ ............................................. A61F 5/48
[52] U.S. Cl. ................................. 128/885; 128/886
[58] Field of Search .......................... 128/846, 885, 128/886; 340/573, 539, 604, 620

[56] References Cited

U.S. PATENT DOCUMENTS

| | | | |
|---|---|---|---|
| 3,831,432 | 8/1974 | Cox | 73/23 |
| 4,590,158 | 5/1986 | Eikman | 435/34 |
| 4,800,370 | 1/1989 | Vetecnik | 128/886 |
| 4,977,906 | 12/1990 | DiScipio | 128/886 |
| 5,122,969 | 6/1992 | Seshimoto | 364/497 |

Primary Examiner—Michael A. Brown
Attorney, Agent, or Firm—Oppenheimer Poms Smith

[57] ABSTRACT

A body waste detector that includes a gas sensor adapted to detect the presence of at least one of gas associated with urine and gas associated with solid body waste and an indicator, operably connected to the gas sensor, adapted to provide an indication that waste has been detected. The detector may be used in combination with a remote alarm unit.

30 Claims, 4 Drawing Sheets

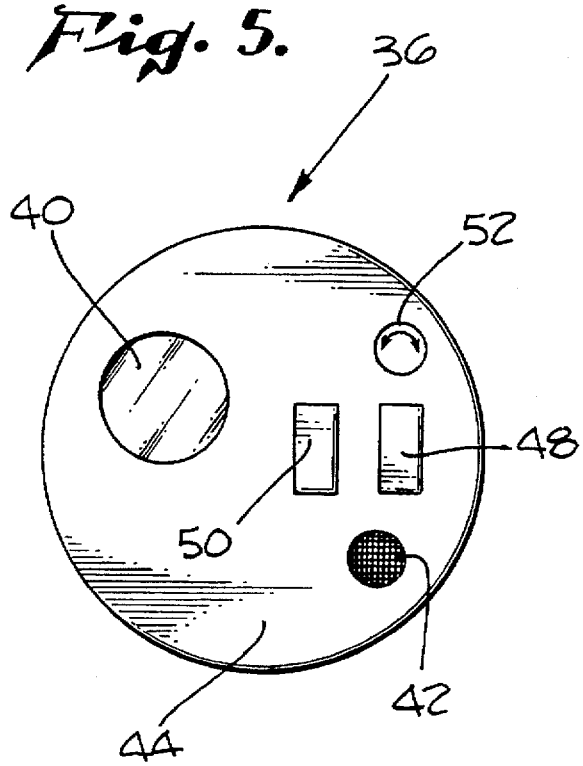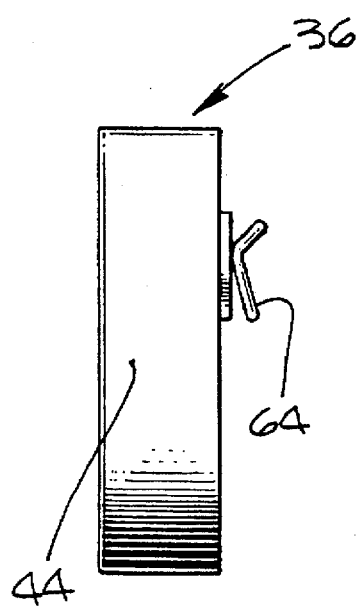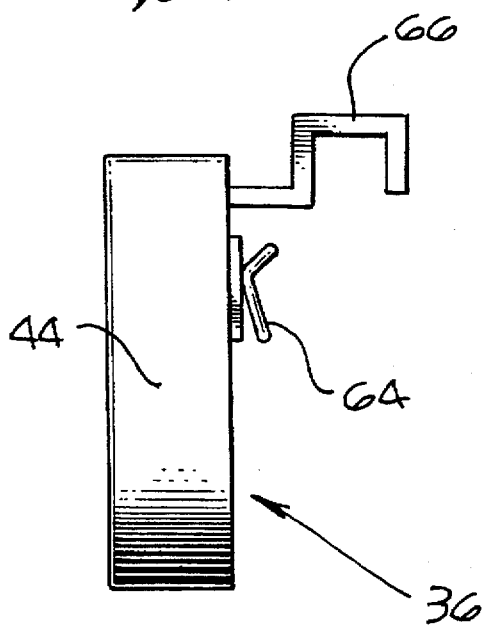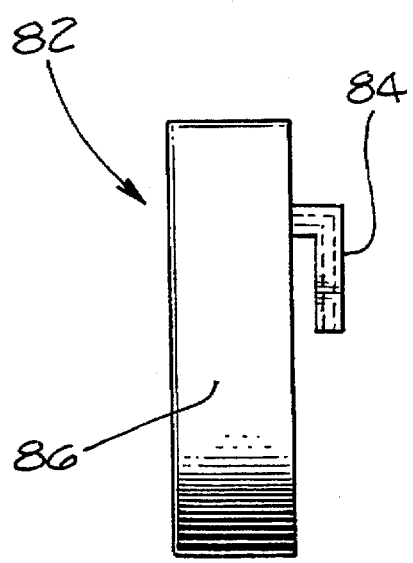

BODY WASTE DETECTION AND ALARM SYSTEM

BACKGROUND OF THE INVENTION

1. Field of Invention

The present invention relates generally to a body waste detection system and, more particularly, to a body waste detection system including a gas detection device.

2. Description of the Related Art

Diaper rash is a common problem for parents with infants. It can also be a problem for those who care for incontinent adults that are unable to fend for themselves. The most common cause of diaper rash is the wearing of wet diapers or clothing for a prolonged period. This can occur because not all babies cry when wet and babies that do cry are not always heard immediately, especially when their parents are in a different room. Adults in hospitals or nursing homes may also have difficulty contacting their care givers.

Over the years, a variety of devices have been introduced for detecting the presence of urine in a diaper or clothing. Such devices include an electrical circuit which is in some way effected by the presence of urine. Typically, the urine provides a conductive path between two electrodes to complete the circuit. These devices also include an audible or visual alarm that is triggered in response to the detection of waste. The alarm provides care givers, such as parents or nurses, with an indication that the diaper or clothing needs to be changed.

The inventor herein has discovered that there are a number of shortcomings associated with the conventional detection and alarm systems that have been introduced heretofore. For example, conventional urine detection devices require physical contact between the urine and the detection device. As a result, the device must either be cleaned after each use, which is inconvenient and time consuming, or be of the disposable variety, which is costly. Additionally, the conventional devices are not designed to detect solid waste.

OBJECT AND SUMMARY OF THE INVENTION

A general object of the present invention is to provide a waste detection device that is superior to those presently known in the art. In particular, one object of the present invention is to provide a body waste detection unit which does not require physical contact between the urine and the device for detection. Another object of the present invention is to detect solid waste.

In accordance with one aspect of the present invention, these and other objectives are accomplished by providing body waste detection unit having a gas sensor that is adapted to detect the presence of at least one of gas associated with urine and gas associated with solid body waste. Because detection is accomplished by monitoring the air adjacent to, for example, a baby's diaper, the need for physical contact between the urine and the detection device is eliminated. As a result, the problems associated with conventional devices, i.e. cleaning and disposal, are eliminated.

Many other features and attendant advantages of the present invention will become apparent as the invention becomes better understood by reference to the following detailed description considered in conjunction with the accompanying drawings.

BRIEF DESCRIPTION OF THE DRAWINGS

Detailed description of the preferred embodiments of the invention will be made with reference to the accompanying drawings.

FIG. 5 is a front view of an alarm unit in accordance with a preferred embodiment of the present invention.

FIG. 6 is a side view of the alarm unit shown in FIG. 5.

FIG. 7 is a side view of the alarm unit shown in FIG. 5.

FIG. 11 is a side view of a detection unit in accordance with another preferred embodiment of the present invention.

DETAILED DESCRIPTION OF THE PREFERRED EMBODIMENTS

The following is a detailed description of the best presently known mode of carrying out the invention. This description is not to be taken in a limiting sense, but is made merely for the purpose of illustrating the general principles of the invention. The scope of the invention is defined solely by the appended claims.

Figure 1:
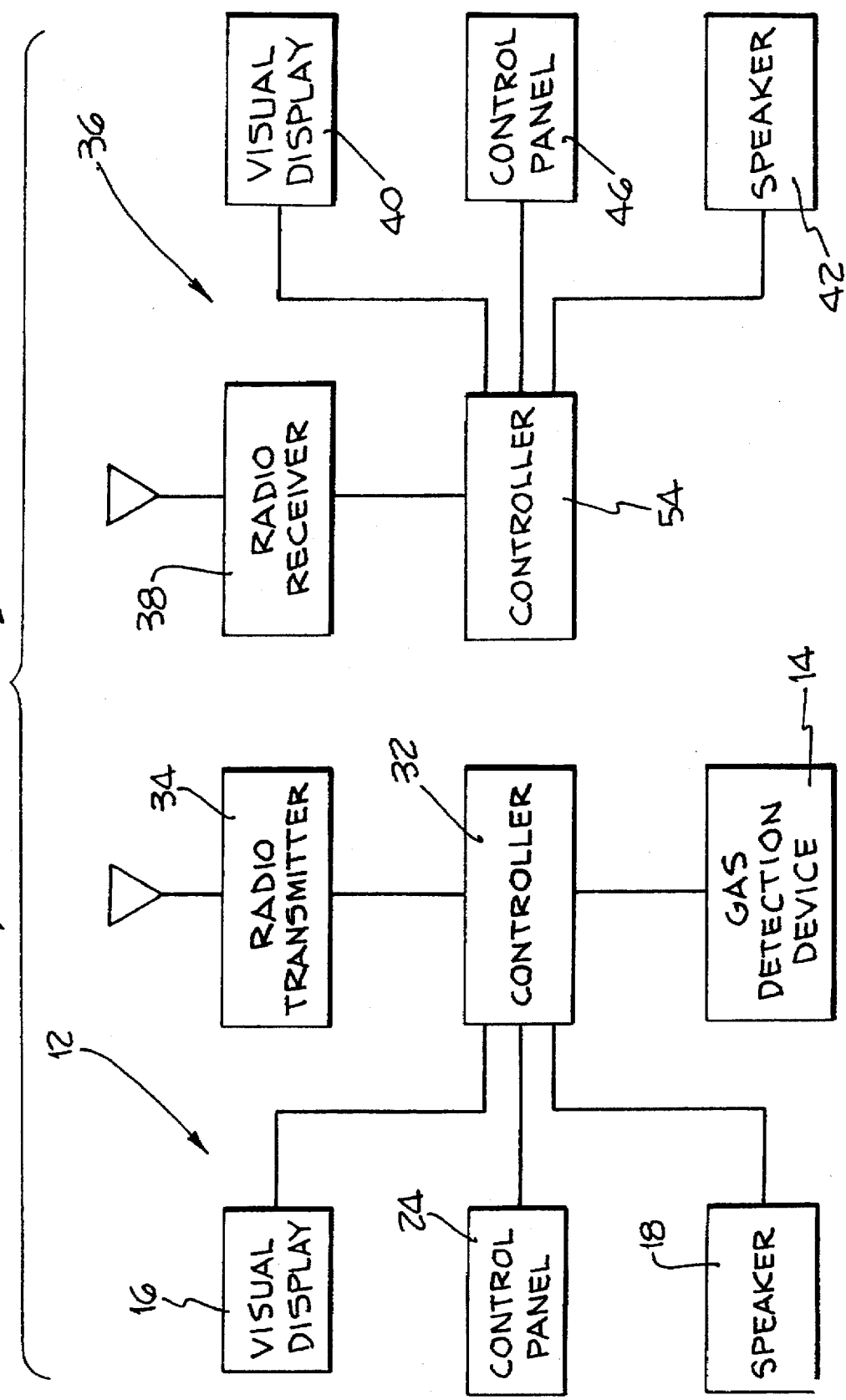
FIG. 1 is a block diagram of a body waste detection and alarm system in accordance with a preferred embodiment of the present invention.
Figure 2:
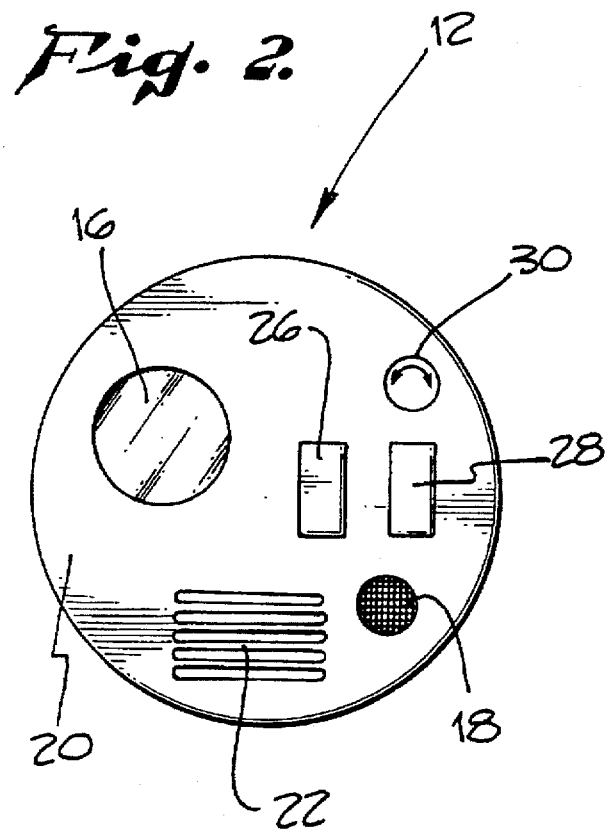
FIG. 2 is a front view of a detection unit in accordance with a preferred embodiment of the present invention.

As illustrated in FIGS. 1 and 2, an exemplary body waste detection and alarm system 10 in accordance with the present invention includes a waste detection unit 12. The detection unit 12 includes a gas detection device 14 which detects the gasses associated with urine or solid body waste (i.e. fecal matter). A visible and/or audible indication that waste is present may be generated by a visual display 16 and a speaker 18 when waste is detected. The visual display 16 and speaker 18 are associated with the exterior of detection unit housing 20, while the gas detection device 14 is located within the housing and exposed to gas by housing slots 22. The housing 20 also includes a control panel 24 which consists of an on/off switch 26, a three way audible/visible/both switch 28, and a knob 30 that allows the user to control the sensitivity of the gas detection device 14. The detection unit 12 is controlled by a controller 32. The controller 32 may be any suitable control device, such as a conventional control circuit. Power for the detection unit is preferably supplied by a battery.

The gas detection device 14 is adapted to detect the gasses (or odors) associated with urine and solid waste. More specifically, the gas detection device will detect the presence of urine gas ($CONH_2$) and ammonium gas ($NH_3$), which are both associated with urine. The gas detection device also detects hydrogen sulfide gas ($H_2S$) from certain enzymes and bacteria as well as volatile hydrogen sulfide organic acid gas (RSH), both of which are associated with solid waste. Preferably, the gas detection device 14 will be triggered by the presence of the combination of $CONH_2$ and $NH_3$ gas and/or by the presence of the combination of $H_2S$ and RSH gas. However, the gas detection device may, if desired, be altered so that it will trigger when it detects these gasses individually. Additionally, in order to prevent false alarms, the detection unit 12 should be configured (or programmed) so that it will not indicate that waste has been detected unless the gasses described above are detected for a predetermined period such as, for example, three minutes.

With respect to structure, the gas detection device 14 may take a variety of forms. For example, the gas detection device may be an electrochemical device that includes optical (or colormetric) cells composed of a normally translucent chemical which becomes cloudy when exposed to a predetermined gas. Such electrochemical devices are commonly used in natural gas, propane and carbon monoxide detectors, such as those manufactured by American Sensors incorporated of North York, Ontario, Canada. Alternatively, semiconductor sensors, which detect the presence of gas based on changes in the surface conductivity of tin oxide, may be used. One manufacturer of semiconductor sensors is Figaro Engineering Incorporated in Japan. Other gas detection devices include spectrum analysis devices and catalyst-based devices.

In accordance with the exemplary detection and alarm system 10, an electromagnetic signal of radio wavelength (preferably an FM signal) will be produced by a radio transmitter 34 in response to the detection of waste. The electromagnetic signal is received by an alarm unit 36 which has a radio receiver 38. The alarm unit/radio receiver range is preferably 50–70 feet, although the range may be altered as desired. This range allows the radio receiver to receive signals from another room.

As illustrated for example in FIGS. 1 and 5, the alarm unit 36 also includes a visual display 40 and speaker 42 which allow the alarm unit to visibly and/or audibly indicate that waste has been detected by the detection unit 12. The visual display 40 and speaker 42 are associated with alarm unit housing 44. The housing also includes a control panel 46 which consists of an on/off switch 48, a three way audible/visible/both switch 50, and a knob 52 that allows the user to control the sensitivity of the radio receiver 38. The alarm unit 36 is controlled by a controller 54 and is preferably powered by a battery.

The signal received by the alarm unit 36 from the detection unit 12 may be such that it merely indicates that the associated baby or adult needs changing. However, the signal (and associated alarm signal emitted by the alarm unit) may be adapted to provide additional information, such as the type of waste that has been detected. A first type of alarm signal from the alarm unit 36, such as one signal followed by a few seconds with no signal, may be used to indicate that urine has been detected. The signal may be a visible signal from the display 40, an audible signal (such as a beep or buzz) from the speaker 42, or both. Similarly, two signals followed by a few seconds with no signal may be used to indicate that solid waste has been detected, and three signals followed by a few seconds with no signal may be used to indicate that both types of waste have been detected. Alternatively, the signal may consist of a periodic beep or buzz with the visual display providing more specific information through a color change, predetermined blinking sequence, numerical indication, etc.

Figure 3:
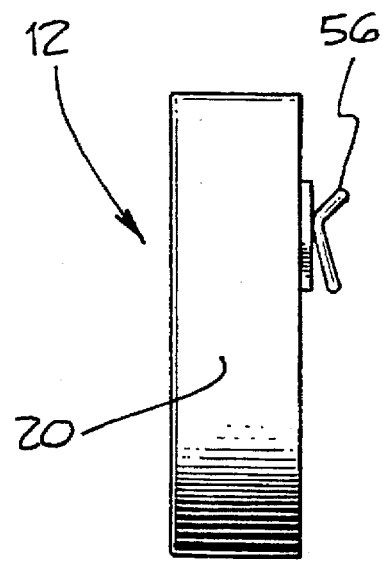
FIG. 3 is a side view of the detection unit shown in FIG. 2.
Figure 4:
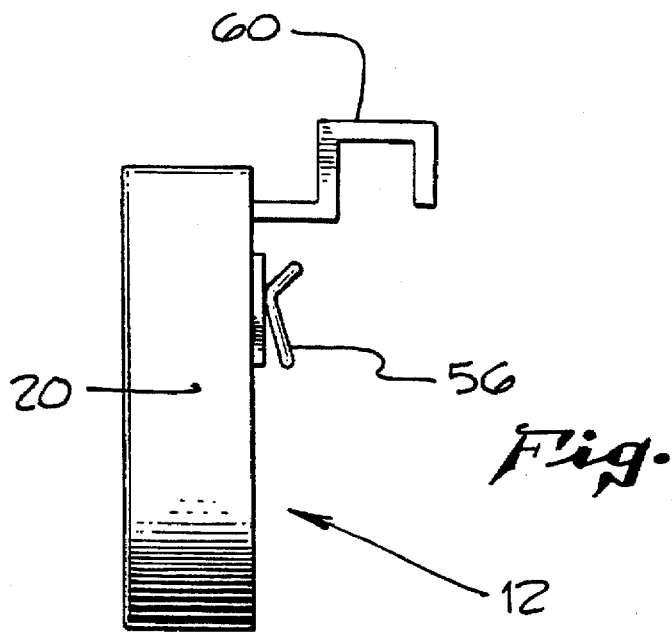
FIG. 4 is a side view of the detection unit shown in FIG. 2.
Figure 8:
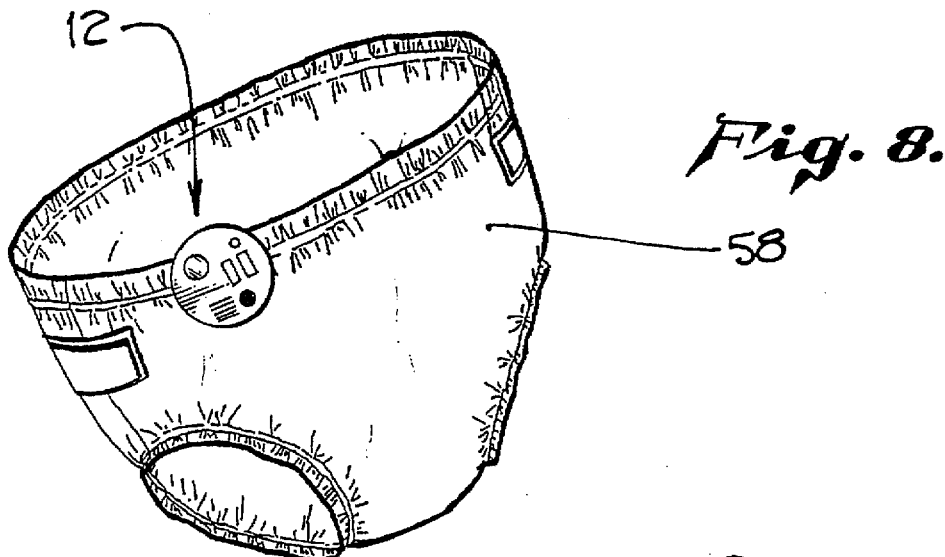
FIG. 8 is a perspective view of a diaper including a preferred embodiment of the present waste detection unit.
Figure 9:
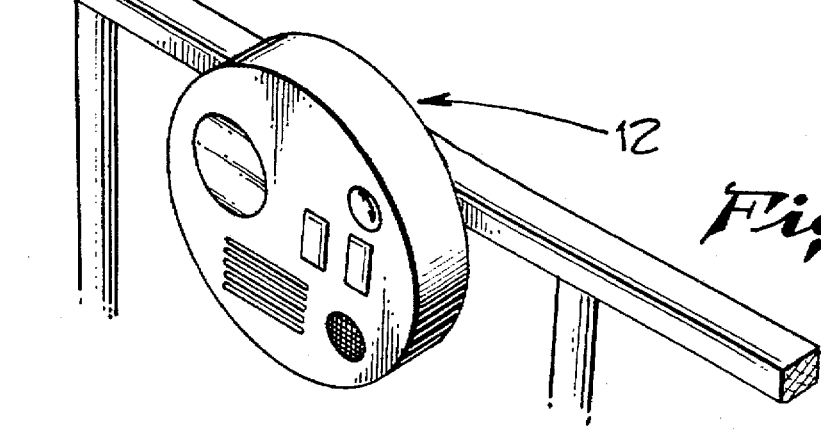
FIG. 9 is a partial perspective view of a crib including a preferred embodiment of the present waste detection unit.

The detection unit 12 may be placed next to the baby or adult in a crib or bed. However, as shown by way of example in FIGS. 3 and 8, the exemplary detection unit housing 20 includes a fastening device, such as a spring biased clip 56, which allows the detection unit to be secured to a diaper 58 or other article of clothing. The clip may, of course, be replaced by other suitable fastening devices such as a safety pin or adhesive tape (commonly sold under the trade name VELCRO™). Turning to FIGS. 4 and 9, a bracket 60 which snap fits into the housing 20 may also be provided if desired.

The bracket 60 allows the detection unit 12 to be secured to a crib 62. The bracket may also be used to secure the detection unit to a bed, bed post, wheel chair, stroller, or any other type of furniture or transport device. The size and shape of the bracket may, of course, be varied to suit particular needs.

Similarly, as shown in FIGS. 6 and 7, the exemplary alarm unit housing 44 includes a spring biased clip 64 that allows the alarm unit to be conveniently secured to an article of clothing, purse, etc. A bracket 66 may also be snap fit into the into the alarm unit housing 44 so that the alarm unit can be secured to a chair or other structure. Here too, the size and shape of the bracket may be varied.

As noted above, the exemplary detection unit 12 includes a knob which allows the sensitivity of the gas detection device 14 to be adjusted. Thus, if the unit is located away from the baby, the sensitivity of the gas detection device 14 may be increased through the use of knob 30. Similarly, if a number of babies are located in close proximity to one another, the sensitivity level may be reduced in order to prevent gas from one baby from triggering the detection unit associated with another.

With respect to dimensions, the exemplary detection unit 12 is preferably from 2 to 4 inches in diameter and approximately 0.5 inch thick. The exemplary alarm unit is approximately 1.5 inches in diameter and 0.5 inch thick. These dimensions may, however, be modified to suit particular needs.

The exemplary body waste detection and alarm system 10 described above includes a single detection unit 12 and a single alarm unit 36. However, a plurality of detection units may be used in combination with a single alarm unit. Here, the alarm unit may produce an audible indication that changing is needed, while the visual display on the detection unit changes color (or blinks, etc.) to indicate to the care giver exactly which person needs changing.

Figure 10:
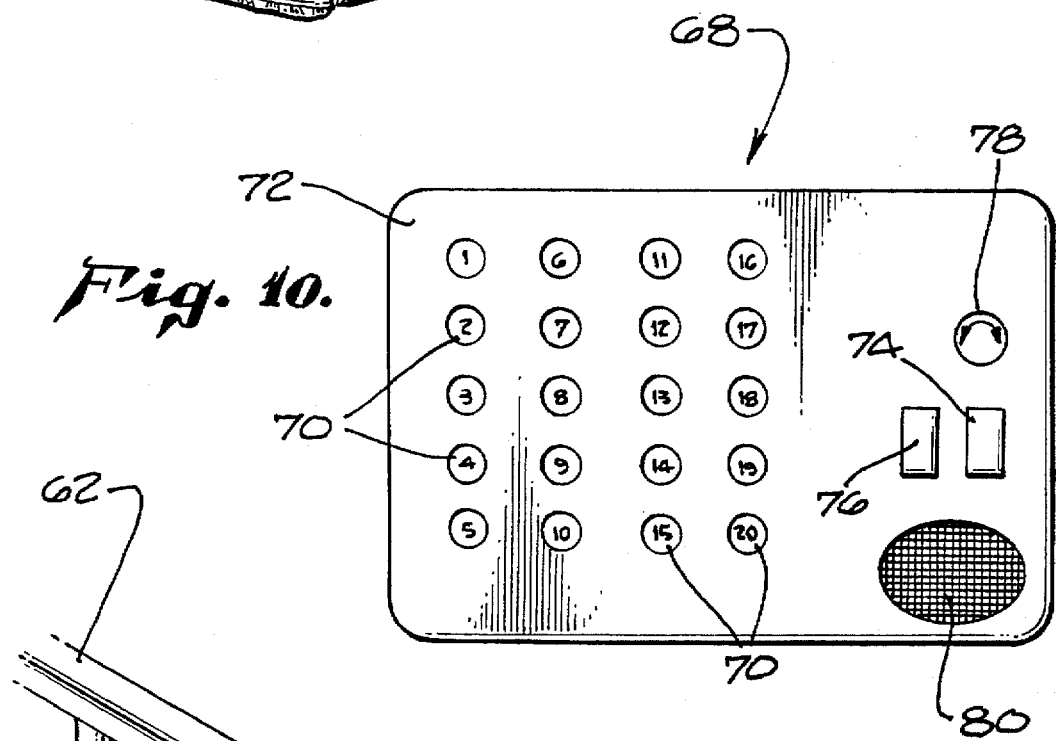
FIG. 10 is a front view of an alarm unit in accordance with another preferred embodiment of the present invention.

An alarm unit 68 for use with a large number of babies or adult patients is shown by way of example in FIG. 10. Each baby or patient is paired with a respective detection unit that produces a signal which, in addition to indicating that changing is required, identifies the detection unit. Here, the exemplary overall system may include up to 20 detection units (numbered 1–20) and the alarm unit 68 includes a series of correspondingly numbered visual indicators 70. The indicators 70 are associated with the exterior of a housing 72, as are an on/off switch 74, three way audible/visible/both switch 76, and knob 78 that allows the user to control the sensitivity of the radio receiver. The alarm unit 68 also includes a speaker 80. When a one or more of the detection units is triggered, the corresponding alarm unit visual indicator 70 will be actuated. If desired, the speaker 80 will also provide an indication that changing is required. If, for example, the detection units are attached to the diapers or cribs of a number of babies in a nursery, then the sensitivity of each unit should be set at a relatively low level to prevent the waste associated with one baby from being detected by the units of those nearby.

As shown by way of example in FIG. 11, a detection unit 82 in accordance with another preferred embodiment of the present invention includes a gas inlet conduit (or tube) 84 which directs gas from within the diaper to the gas detection device within the detection unit housing 86. Such an inlet conduit is especially useful in conjunction with diapers having elastic lined waist and leg apertures which may trap gas within the diaper. When the baby breathes or moves, the volume within the diaper is often reduced, thereby forcing gas though the inlet conduit 84 and into the detection unit. Here, the inlet conduit 84 is in the form of a hollow clip which secures the detection unit to the diaper. The inlet conduit and clip may, however, be configured as separate structural elements.

Although the present invention has been described in terms of the preferred embodiment above, numerous modifications and/or additions to the above-described preferred embodiments would be readily apparent to one skilled in the art. By way of example, but not limitation, a vibrating device (such as those used in pagers) may be incorporated into the alarm unit and if desired, used in place of the audible and/or visible indicators. A test/reset button may be provided on the detection unit. The alarm unit may also be equipped with a small handle. It is intended that the scope of the present invention extends to all such modifications and/or additions and that the scope of the present invention is limited solely by the claims set forth below.

What is claimed is:

1. A body waste detector, comprising:
   a housing defining at least one gas inlet aperture;
   a gas sensor located substantially within the housing and adapted to detect the presence of at least one of gas associated with urine and gas associated with solid body waste; and
   an indicator, operably connected to the gas sensor, adapted to provide an indication that waste has been detected.

2. A body waste detector as claimed in claim 1, wherein the housing includes a fastener adapted to secure the housing to an article of clothing.

3. A body waste detector as claimed in claim 2, wherein the article of clothing comprises a diaper.

4. A body waste detector as claimed in claim 2, wherein the fastener comprises a spring-biased clip.

5. A body waste detector as claimed in claim 1, wherein the housing includes a bracket adapted to mount the housing on at least one of a piece of furniture and a transport device.

6. A body waste detector as claimed in claim 1, wherein the gas associated with urine comprises $CONH_2$ in combination with $NH_3$.

7. A body waste detector as claimed in claim 1, wherein the gas associated with solid body waste comprises $H_2S$ in combination with RSH.

8. A body waste detector as claimed in claim 1, wherein the gas sensor comprises an electrochemical sensor.

9. A body waste detector as claimed in claim 1, wherein the gas sensor comprises a semiconductor sensor.

10. A body waste detector as claimed in claim 1, wherein the indicator comprises a visual display.

11. A body waste detector as claimed in claim 1, wherein the indicator comprises an audible indicator.

12. A body waste detector as claimed in claim 1, wherein the indicator comprises a transmitter.

13. A body waste detector as claimed in claim 1, wherein the gas sensor will not produce an indication that waste has been detected until at least one of gas associated with urine and gas associated with solid body waste has been detected for a predetermined period.

14. A body waste detector as claimed in claim 1, further comprising:
   an inlet conduit associated with the inlet aperture.

15. A body waste detection and alarm system, comprising:
   a body waste detection unit including a gas sensor and adapted to detect the presence of at least one of gas associated with urine and gas associated with solid body waste, and a transmitter operably connected to the gas sensor and adapted to transmit a signal in response to a detection of gas by the gas sensor; and
   an alarm unit including a receiver adapted to receive the signal from the body waste detection unit transmitter, and an indicator operably connected to the receiver and adapted to provide an indication that waste has been detected in response to a reception of the signal.

16. A body waste detection and alarm system as claimed in claim 15, wherein the alarm unit indicator comprises a visual display.

17. A body waste detection and alarm system as claimed in claim 15, wherein the alarm unit indicator comprises an audible indicator.

18. A body waste detection and alarm system as claimed in claim 15, wherein the body waste detection unit comprises a plurality of body waste detection units and the alarm unit indicator includes a plurality of indicators respectively corresponding to the plurality of body waste detection units.

19. A body waste detection and alarm system as claimed in claim 15, wherein the body waste detection unit includes a housing, the gas sensor is located substantially within the housing, and the housing defines at least one gas inlet aperture.

20. A body waste detection and alarm system as claimed in claim 19, wherein the body waste detection unit housing includes a fastener adapted to secure the housing to an article of clothing.

21. A body waste detection and alarm system as claimed in claim 19, wherein the body waste detection unit housing includes a bracket adapted to mount the housing on at least one of a piece of furniture and a transport device.

22. A body waste detection and alarm system as claimed in claim 15, wherein the alarm unit includes a housing having a fastener.

23. A body waste detection and alarm system as claimed in claim 15, wherein the alarm unit includes a bracket adapted to mount the housing on a structure.

24. A body waste detection and alarm system as claimed in claim 15, wherein the gas associated with urine comprises $CONH_2$ in combination with $NH_3$.

25. A body waste detection and alarm system as claimed in claim 15, wherein the gas associated with solid body waste comprises $H_2S$ in combination with RSH.

26. A body waste detection and alarm system as claimed in claim 15, wherein the gas sensor comprises an electrochemical sensor.

27. A body waste detection and alarm system as claimed in claim 15, wherein the gas sensor comprises a semiconductor sensor.

28. A body waste detection and alarm system as claimed in claim 15, wherein the gas sensor will not produce an indication that waste has been detected until at least one of gas associated with urine and gas associated with solid body waste has been detected for a predetermined period.

29. A body waste detection and alarm system as claimed in claim 15, wherein the signal comprises a radio signal.

30. A body waste detection and alarm system as claimed in claim 15, wherein the body waste detection unit includes a housing, the gas sensor is located substantially within the housing, the housing defines at least one gas inlet aperture and an inlet conduit is associated with the inlet aperture.

* * * * *